United States Patent
Bender et al.

(10) Patent No.: US 9,522,858 B2
(45) Date of Patent: Dec. 20, 2016

(54) TRANSALKYLATION SYSTEM

(71) Applicant: ExxonMobil Chemical Patents Inc., Baytown, TX (US)

(72) Inventors: Timothy P. Bender, Houston, TX (US); Xiaobo Zheng, Houston, TX (US); Robert G. Tinger, Friendswood, TX (US); Todd E. Detjen, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/786,740

(22) PCT Filed: Apr. 22, 2014

(86) PCT No.: PCT/US2014/035027
§ 371 (c)(1),
(2) Date: Oct. 23, 2015

(87) PCT Pub. No.: WO2014/193563
PCT Pub. Date: Dec. 4, 2014

(65) Prior Publication Data
US 2016/0075618 A1    Mar. 17, 2016

Related U.S. Application Data

(60) Provisional application No. 61/829,360, filed on May 31, 2013.

(51) Int. Cl.
| | | |
|---|---|---|
| *C07C 6/12* | (2006.01) | |
| *C07C 2/66* | (2006.01) | |
| *C07C 4/14* | (2006.01) | |
| *C07C 6/06* | (2006.01) | |
| *C07C 2/86* | (2006.01) | |
| *C07C 4/18* | (2006.01) | |
| *C07C 7/148* | (2006.01) | |
| *B01J 29/80* | (2006.01) | |

(Continued)

(52) U.S. Cl.
CPC ............... *C07C 6/06* (2013.01); *B01J 19/245* (2013.01); *B01J 29/80* (2013.01); *C07C 2/864* (2013.01); *C07C 4/06* (2013.01); *C07C 4/12* (2013.01); *C07C 4/18* (2013.01); *C07C 6/126* (2013.01); *C07C 7/14858* (2013.01); *B01J 29/44* (2013.01); *B01J 29/48* (2013.01); *B01J 29/7469* (2013.01); *B01J 29/7869* (2013.01); *C07C 2529/40* (2013.01); *C07C 2529/44* (2013.01); *C07C 2529/70* (2013.01); *C07C 2529/74* (2013.01); *Y02P 20/52* (2015.11)

(58) Field of Classification Search
CPC ................ C07C 2/66; C07C 4/14; C07C 6/12
USPC ............... 585/323, 318, 483, 488, 474, 470, 585/469, 585/446
See application file for complete search history.

(56) References Cited

U.S. PATENT DOCUMENTS 5,030,787 A    7/1991   Absil et al.
5,763,720 A    6/1998   Buchanan et al.
(Continued)

FOREIGN PATENT DOCUMENTS

WO    WO2012/074613    6/2012
WO    WO2013/173755    11/2013

*Primary Examiner* — Thuan D Dang (57) ABSTRACT

The invention relates to a transalkylation system to convert feedstreams containing benzene and/or toluene (C7- aromatic hydrocarbons) and feedstreams containing C9+ aromatic hydrocarbons into a product stream comprising xylenes.

12 Claims, 3 Drawing Sheets

(51) Int. Cl.
*B01J 19/24* (2006.01)
*C07C 4/06* (2006.01)
*C07C 4/12* (2006.01)
*B01J 29/44* (2006.01)
*B01J 29/48* (2006.01)
*B01J 29/74* (2006.01)
*B01J 29/78* (2006.01)

(56) References Cited

U.S. PATENT DOCUMENTS

| | | | |
|---|---|---|---|
| 5,942,651 A | 8/1999 | Beech, Jr. et al. | |
| 6,867,340 B2 | 3/2005 | Oh et al. | |
| 6,893,624 B2 | 5/2005 | Lai et al. | |
| 7,148,391 B1 | 12/2006 | Buchanan et al. | |
| 7,439,204 B2 | 10/2008 | McMinn et al. | |
| 7,553,791 B2 | 6/2009 | McMinn et al. | |
| 7,629,499 B2 | 12/2009 | Serra Alfaro et al. | |
| 7,663,010 B2 | 2/2010 | Levin | |
| 8,071,828 B2 * | 12/2011 | Cao | C07C 2/66 585/319 |
| 8,163,966 B2 | 4/2012 | Levin | |
| 8,183,424 B2 | 5/2012 | Levin et al. | |
| 8,586,809 B2 | 11/2013 | Beech, Jr. et al. | |
| 8,609,918 B2 | 12/2013 | Matsushita et al. | |
| 8,772,564 B2 | 7/2014 | Matsushita et al. | |
| 8,822,363 B2 | 9/2014 | Levin et al. | |
| 9,079,163 B2 | 7/2015 | Nakaoka et al. | |
| 9,162,942 B2 | 10/2015 | Beech, Jr. et al. | |
| 2005/0027151 A1 * | 2/2005 | Ghosh | C07C 2/864 585/467 |

* cited by examiner

FIG. 2D

TRANSALKYLATION SYSTEM

PRIORITY CLAIM

This application is a National Stage Application of International Application No. PCT/US2014/035027, filed Apr. 22, 2014, which claims the benefit of and priority to U.S. Provisional Application No. 61/829,360, filed May 31, 2013, the disclosures of which are incorporated by reference in their entireties.

FIELD OF THE INVENTION

The invention relates to a transalkylation system to convert feedstreams containing benzene and/or toluene (C7− aromatic hydrocarbons) and feedstreams containing C9+ aromatic hydrocarbons into a product stream comprising xylenes.

BACKGROUND OF THE INVENTION

The manufacture of xylene using transalkylation processes utilize one or more catalysts to convert feed streams containing benzene and/or toluene (collectively, C7− aromatic hydrocarbons) and feed streams containing heavy aromatics, i.e., C9+ aromatic hydrocarbons, into a xylene-containing product stream. The demand for xylenes, particularly paraxylene, has increased in proportion to the increase in demand for polyester fibers and film. Supplying the ever-increasing demand has required solving many problems in the production of paraxylene by transalkylation, such as discussed in U.S. Pat. Nos. 5,030,787; 5,763,720; 5,942,651; 6,893,624; 7,148,391; 7,439,204; 7,553,791; 7,663,010; 8,071,828; 8,163,966; 8,183,424; U.S. Patent Publication Nos. 2010-0298117 and 2012-0024755; U.S. patent application Ser. No. 13/811,403; and U.S. Provisional Patent Application Nos. 61/418,212 and 61/496,262. The value of the product is so great that these processes still merit improvement and there is constant research in this area.

Figure 1A:
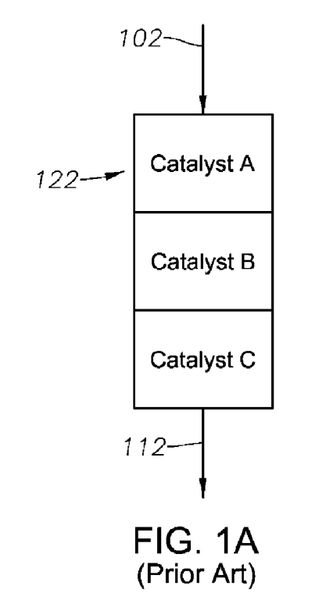
FIGS. 1A-1D illustrate schematically reactor systems for transalkylation according to the prior art.
Figure 1B:
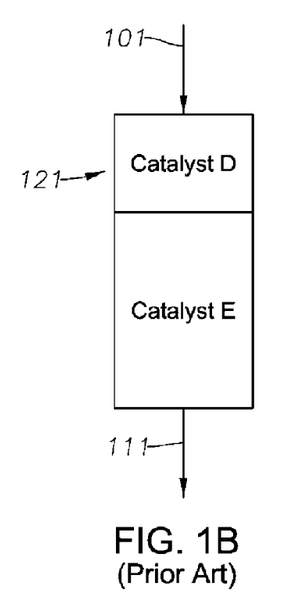
Figure 1C:
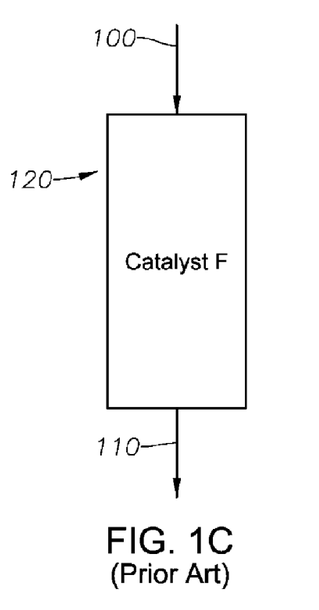

A transalkylation system utilizing a single catalyst for transalkylation is illustrated schematically in FIG. 1C, wherein catalyst F is contacted in reactor 120 with feedstream 100 comprising the C7− aromatic hydrocarbons and C9+ aromatic hydrocarbons to produce product 110 comprising xylenes. In a specific example, the catalyst F is ZSM-12 comprising a hydrogenation component and a support, such as $Al_2O_3$. The hydrogenation component may be at least one metal or compound thereof, from Groups 6-12 of the Periodic Table.

A dual catalyst system for transalkylation is illustrated schematically in FIG. 1B. In FIG. 1B a feedstream 101 comprising C7− aromatic hydrocarbon and C9+ aromatic hydrocarbon first contacts catalyst D in reactor 121 and then the product of the contact with catalyst D contacts catalyst E, providing product 111 comprising xylenes. One example of a two-catalyst system D followed by E, respectively, is ZSM-12 comprising a hydrogenation component and a support, followed by a catalyst comprising ZSM-5 without a hydrogenation component. In this case the presence of the second catalyst is found to improve purity by cracking certain undesired co-boilers that make separation of the desired product(s) more difficult. A second example of a two-catalyst system D followed by E, respectively, is ZSM-12 comprising a hydrogenation component followed by ZSM-12 comprising a hydrogenation component. In this case the ZSM-5 and hydrogenation component facilitates de-alkylation of C10+ aromatic hydrocarbons to enhance recovery of desired products and/or reduce aging of the downstream ZSM-12 component.

A three-catalyst system for transalkylation is illustrated schematically in FIG. 1A. In FIG. 1A a feedstream 102 comprising C7− aromatic hydrocarbons and C9+ aromatic hydrocarbons contacts catalysts A, then catalyst B, then catalyst C, to produce product 112 comprising xylenes. One example of such a three-catalyst system is ZSM-5 with a hydrogenation component, followed by ZSM-12 comprising a hydrogenation component, and then ZSM-5 without a hydrogenation component, where again the ZSM-5 as the third component cracks certain undesired co-boilers to enhance purity of the final product.

A typical feed to such process can be any conventional $C_8+$ aromatic hydrocarbon feed available in a petroleum or petrochemical refinery, such as a catalytic reformate, FCC or TCC naphtha, or a xylene isomerizate from which heptanes and lighter components have been removed. The feed is initially passed through a xylenes fractionation column or columns to remove the $C_8$ aromatic components from the feed and leave a $C_9+$ aromatic hydrocarbon-rich fraction which can then be fed to a transalkylation reactor for reaction with benzene or toluene in the presence of a transalkylation catalyst system, such as described above, to produce lighter aromatic products, primarily benzene, toluene, and xylenes (collectively, "BTX"). These components can then be separated by methods well-known in the art, and all or a portion of the benzene and toluene can be recycled through the transalkylation system.

Figure 1D:
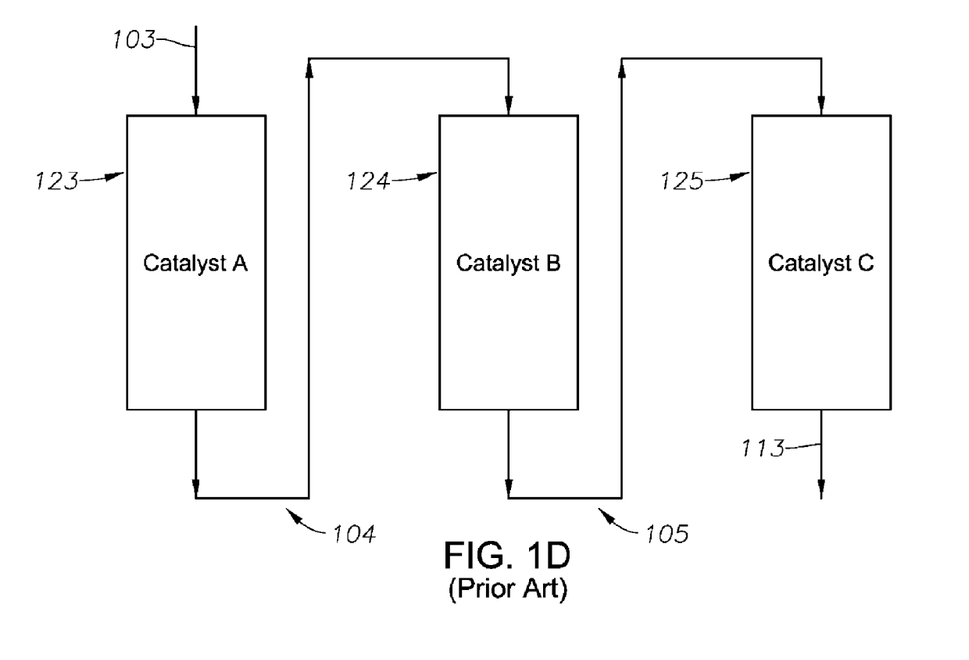

In the case of the use of multiple catalysts, the first, second and optional third catalyst beds may be located in separate reactors, such as illustrated schematically in FIG. 1D. FIG. 1D illustrates an alternative to FIG. 1A. In FIG. 1D, feedstream 103 contacts catalyst A in first reactor 123, then catalyst B in second reactor 124, and finally catalyst C in third reactor 125, providing product 112 comprising xylenes.

In the case of multiple catalysts in a single reactor, the catalysts will typically be separated from each other by spacers or by inert materials, such as, alumina balls or sand. Alternatively, the first and second catalyst beds could be located in one reactor and the third catalyst bed (when present) is located in a different reactor. As a further alternative, the first catalyst bed could be located in one reactor and the second and third catalyst beds (when present) are located in a different reactor. In all situations illustrated, the separate catalysts such as A, B, and C in both FIG. 1A and FIG. 1D are not mixed and the hydrocarbon feedstocks and hydrogen are arranged to contact the first catalyst bed prior to contacting the second catalyst bed. Similarly, if the third catalyst bed is present, the hydrocarbon feedstocks and hydrogen are arranged to contact the second catalyst bed prior to contacting the third catalyst bed. However, numerous systems are known wherein at least two different catalysts are mixed together in a single bed. Likewise, while the FIGS. 1A-1D show axial flow reactors, it will be appreciated by one of skill in the art that radial flow reactors could also be used, alone or in combination with axial flow reactors.

U.S. Pat. No. 7,629,499 describes a process for transalkylation comprising: (a) introduction of alkyl-aromatic feedstock at the inlet of a first reaction zone to contact a first zeolite catalyst to obtain an effluent; (b) introduction of at least a portion of the effluent from the first reaction zone and a feedstock that contains benzene and toluene to the inlet of a second reaction zone that contains a second zeolite catalyst to obtain a second effluent; and (c) separation of at least a portion of the second effluent. An improvement in xylene yield is said to be achieved by this method. Hydrogen is introduced at each inlet.

Catalyst life and extent of aromatic ring loss reactions across the reactor are two important performance characteristics for transalkylation catalysts and catalyst systems. Typically it is ideal to maximize catalyst life, while at the same time reducing the extent of aromatic ring loss reactions (which reduces yield), and generally increasing the desired products (paraxylene in particular) and decreased the undesired products (such as benzene co-boilers).

The present invention uses two or more separate staged feed locations to the transalkylation reactor system in order to improve yields (including reduced ring loss reaction) and to increase catalyst life and attenuates the introduction of hydrogen through the two or more separate staged feed locations to effect improved results.

SUMMARY OF THE INVENTION

The invention is directed to a process for transalkylation of C7− and C9+ aromatic hydrocarbons by contact with a catalyst or catalyst system to produce a product stream comprising xylenes, wherein two or more separate staged feed locations are provided to at least one transalkylation reactor. Hydrogen gas is selectively introduced through one or more of the staged feed locations. In embodiments improvements include at least one of improved yields and increased catalyst life.

As used herein the term "catalyst system" means at least two different catalysts, which may be mixed together or separated, and may be in single or multiple reactors in series or in parallel, or any combination thereof.

In a preferred embodiment of this invention, a first feedstream comprising C9+ aromatic hydrocarbon stream, preferably heavy-aromatics-rich stream, e.g., 50+ wt %, more preferably 80+ wt % C9+ aromatic hydrocarbons, is fed to the top bed of the reactor, which is preferably a fixed bed reactor comprising a catalyst or catalyst system optimized for dealkylation and/or heavy aromatic hydrocarbon conversion, and a second feedstream comprising benzene and/or toluene, preferably benzene and/or toluene-rich feed, e.g., 50+ wt %, more preferably 70+ wt % C7− aromatic hydrocarbons, is fed directly into the second bed of the reactor, which is preferably a fixed bed reactor comprising a catalyst or catalyst system optimized for benzene and/or toluene conversion and more preferably also an additional conversion of C9+ aromatic hydrocarbon, such as up to 30 wt % conversion. The first and second beds may be in separate reactors or they may be in the same reactor but are not mixed. In preferred embodiments, the amount of hydrogen present, if any, is in amounts sufficient to saturate at least a portion of the olefins formed in the top bed of the reactor while minimizing saturation of the aromatic species.

Surprisingly, advantages realized by the present invention include, in embodiments, as least one or more of reduced top bed ring loss reactions, increased xylene yields via disproportionation mechanism versus dealkylation mechanism, increased benzene byproduct purity, and increased reactor top bed cycle length.

These and other objects, features, and advantages will become apparent as reference is made to the following detailed description, preferred embodiments, examples, and appended claims.

BRIEF DESCRIPTION OF THE DRAWINGS

In the accompanying drawings, like reference numerals are used to denote like parts throughout the several views.

DETAILED DESCRIPTION OF THE INVENTION

According to the invention, a C9+ aromatic hydrocarbon feed stream is provided to the inlet of a reactor system comprising a first catalyst for dealkylation of said C9+ aromatic hydrocarbons, preferably C10+ aromatic hydrocarbons, more preferably C10+ aromatic hydrocarbons having C2+ alkyl groups, such as C2-C4 alkyl groups, to make aromatic hydrocarbons having less side groups, such as C9− aromatic hydrocarbons, with co-production of olefins, such as C2-C4 olefins, and, in the presence of hydrogen gas in an amount sufficient to hydrogenate said olefins and minimize saturation of aromatic rings, convert at least a portion of said olefins to alkanes, such as C2-C4 alkanes. The product of this reaction, comprising C9 aromatic hydrocarbons and a reduced amount of C10+ aromatic hydrocarbons, preferably a reduced amount of C10+ aromatic hydrocarbons having C2+ side chains when compared with said C9+ aromatic hydrocarbon feed stream, is then introduced, along with a C7− aromatic feed stream (benzene and/or toluene), to a second catalyst for transalkylation of benzene and/or toluene with C9+ to produce an effluent comprising xylenes. The C7− feed stream is introduced to the second catalyst through a second inlet downstream of said first inlet, preferably to minimize contact with said first catalyst system in the presence of hydrogen. Hydrogen gas may be provided through said second inlet with said C7− aromatic feed stream, and/or separately through an inlet downstream of said first inlet. The xylene effluent may then contact yet a third catalyst, such as a catalyst suitable to crack non-aromatic species, such as cyclohexane.

Pilot plant data on two-bed systems wherein the feeds (aromatic hydrocarbons and hydrogen gas) are treated by conventional reactor systems wherein the entire feed (C7− and C9+ aromatic hydrocarbons) is provided only to the top catalyst bed demonstrates that 40-80% of undesired ring loss reactions across the reactor occur in the top bed of the reactor. Secondly, pilot plant data demonstrates that toluene and benzene are net created (not converted) across the top bed. Therefore, benzene and toluene in the feed to the top bed provide a net negative yield impact to the top bed because they dilute the partial pressure of the reactive C9+ aromatic hydrocarbons. By removing/minimizing benzene and/or toluene and/or hydrogen feed to the top bed or by staging the benzene and/or toluene and/or hydrogen feed to further down the top bed, the C9+ dealkylation kinetics will be increased resulting in the ability to achieve higher conversion at constant temperature and weight hourly space velocity (feed rate/catalyst weight). This reduces the amount of catalyst needed to perform the top bed dealkylation reactions. Pilot plant data also demonstrates that at constant conversion ring loss reactions are reduced with increased WHSV. In addition, reduced toluene and benzene composition in the top bed will drive higher net benzene and toluene production across the top bed which will increase the second bed benzene/toluene to C9+ aromatic ratio, which in turn will drive higher xylene yields via disproportionation across the second bed of the reactor.

Moreover, ring loss reaction kinetics are favored at lower temperatures, whereas dealkylation reactions are favored at relatively higher temperatures. By introducing the benzene/ toluene rich stream downstream of the top bed or staged lower into the top bed, flexibility is gained to operate the top bed at higher than typical starting temperatures (740-800° F. versus 730-740° F. typical; about 393-427° C. versus 388-393° C.) and cool the second bed temperature to normal operating temperatures (750-770° F.; about 399-410° C.) by introducing the benzene/toluene feed stream at lower than target second bed reactor temperature (700-740° F.; about 371-427° C.) to cool the top bed effluent.

Furthermore, a portion of the total hydrogen feed to the reactor can also be staged with or without the benzene/ toluene rich stream lower into the top bed and/or below the top bed of the reactor. Hydrogen serves two main functions in the reactor. First hydrogen is needed to saturate olefinic gas created in the dealkylation reactions (predominantly occurring in top reactor bed). Saturating the olefinic gas prevents these molecules from undergoing undesired reactions with aromatic compounds. Secondly, hydrogen is fed to the reactor to reduce coke production rates and extend the catalyst life. However, as the partial pressure of hydrogen to the reactor increases, undesired ring loss reaction yields increase. Staging a portion of the hydrogen lower into the top bed and/or below the top bed of catalyst will result in reduced hydrogen partial pressure at the reactor inlet, and more uniform hydrogen partial pressure through-out the reactor. The lower hydrogen partial pressure at the reactor inlet will reduce ring loss reactions which are kinetically more favored at the entry to the top reactor bed because it operates at lower temperatures than the rest of the reactor (dealkylation is exothermic, resulting in net temperature increase across the reactor). In addition, staged hydrogen injection lower into the top bed and/or below the top bed can be managed to elevate hydrogen partial pressure in the lower sections of the reactor to control/reduce aging of the catalyst relative to traditional methods of injecting all hydrogen at the inlet to the top reactor bed or even in a system where hydrogen is injected at two points in the system but not controlled or attenuated.

In addition, experimental data shows that benzene byproduct purity increases as the hydrogen to hydrocarbon ratio is reduced to the reactor. Benzene byproduct purity can be monitored downstream of the catalyst system for transalkylation, which would be recognized by one of skill in the art in possession of the present disclosure. Staged hydrogen injection reduces the localized hydrogen to hydrocarbon ratio in the top bed and potentially a portion of the bottom bed of the reactor, thus reducing the benzene co-boiler byproduct yields that result in reduced benzene byproduct purity. By operating the reactor with staged feed as discussed above, with higher operating top bed temperature (740-800° F.; about 393-427° C.) and typical second bed temperatures (730-750° F.; 388-393° C.), undesired ring loss reaction yields across the reactor are reduced, xylene yields are increased, benzene byproduct purity is increased, and top bed catalyst life can be extended due to improved reaction kinetics.

In the transalkylation reaction, temperatures exceeding 450° C. lead to higher catalyst deactivation rates due to increased paring reaction rates and coke condensation. By quenching the effluent from the first reaction with toluene and/or hydrogen, the temperature of the transalkylation reaction can be controlled below this critical 450° C., should the top bed require higher operating temperature than the transalkylation reactor. Alternatively, a heat exchanger can be placed between the top bed and the transalkylation reactor to further adjust the operating temperature of the transalkylation reactor.

One specific example of a transalkylation system that can benefit from the present invention has been described in PCT/US2012/039136, wherein the combined C7− and C9+ aromatic hydrocarbon feed contacts a catalyst bed comprising a molecular sieve having a Constraint Index in the range of about 3 to about 12, such as ZSM-5, and at least one hydrogenation component, which is at least one metal or compound thereof of Groups 6 to 12 of the Periodic Table of the Elements, such as platinum, palladium, iridium, rhenium, and mixtures thereof, generally present in an amount from about 0.01 to about 10 wt. % of the catalyst composition, the first catalyst bed maintained under conditions effective to dealkylate aromatic hydrocarbons containing $C_2+$ alkyl groups in the heavy aromatic feedstock and to saturate the resulting $C_2+$ olefins. Suitable conditions for operation of the first catalyst bed comprise a temperature in the range of about 100 to about 800° C., preferably about 300 to about 500° C., a pressure in the range of about 790 to about 7000 kPa-a, preferably about 2170 to 3000 kPa-a, a $H_2$:HC molar ratio in the range of about 0.01 to about 20, preferably about 1 to about 10, and a WHSV in the range of about 0.01 to about 100 $hr^{-1}$, preferably about 2 to about 20 $hr^{-1}$. Modifying this catalyst system with the findings of the present invention, the first bed should operate no higher than 450 C and have a much lower H2:HC molar ratio, e.g., below 1.5:1.

The product of the first catalyst bed is then contacted with a second catalyst bed comprising a molecular sieve having a constraint index less than 3, such as ZSM-12, and at least one hydrogenation component, which is at least one metal or compound thereof of Groups 6 to 12 of the Periodic Table of the Elements, such as platinum, palladium, iridium, rhenium, and mixtures thereof, generally present in an amount from about 0.01 to about 10 wt. % of the catalyst composition, the second catalyst bed maintained under conditions effective to transalkylate $C_9+$ aromatic hydrocarbons with the C7− aromatic hydrocarbons. Suitable conditions for operation of the second catalyst bed comprise a temperature in the range of about 100 to about 800° C., preferably about 300 to about 500° C., a pressure in the range of about 790 to about 7000 kPa-a, preferably about 2170 to 3000 kPa-a, a $H_2$:HC molar ratio in the range of about 0.01 to about 20, preferably about 1 to about 10, and a WHSV in the range of about 0.01 to about 100 $hr^{-1}$, preferably about 1 to about 10 $hr^{-1}$. Again, modifying this second bed with the finding of the present invention, the temperature should be no higher than 450° C.

Where present, the third catalyst bed is maintained under conditions effective to crack non-aromatic cyclic hydrocarbons in the effluent from the second catalyst bed comprising a third molecular sieve having a Constraint Index from about 1 to 12, such as ZSM-5. No hydrogenation component is present in this optional third catalyst bed. Suitable conditions for operation of the third catalyst bed comprise a temperature in the range of about 100 to about 800° C., preferably about 300 to about 500° C., a pressure in the range of about 790 to about 7000 kPa-a, preferably about 2170 to 3000 kPa-a, a $H_2$:HC molar ratio in the range of about 0.01 to about 20, preferably about 1 to about 10, and a WHSV in the range of about 0.01 to about 100 $hr^{-1}$, preferably about 1 to about 50 $hr^{-1}$.

The invention may be better understood by reference to the following detailed examples, illustrated schematically in FIGS. 2A-2D.

Figure 2A:
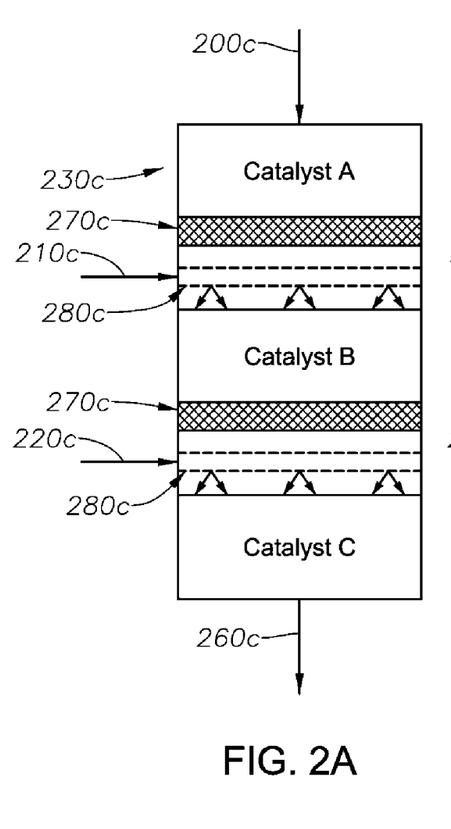
FIGS. 2A-2D illustrate schematically embodiments of the reactor systems for transalkylation according to the present invention.

FIG. 2A shows reactor 230*c* from the perspective of a side view, with conduit 200*c* at the top of the structure providing a feed to the reactor 230*c* so as to flow, such as by gravity, down the reactor 230*c* and out conduit 260*c* at the bottom, as reactor effluent, and containing a catalyst system comprising catalyst A, catalyst B, and catalyst C. Plural grid structures 270*c*, which may be of the type conventional in the art, and which may be the same or different throughout the reactor, are provided to support the solid catalysts A and B, and also allow liquid and gas flowing down the reactor 230*c* to pass through and contact catalyst B. One or more of the grid structures 270*c* may be used to introduce hydrogen gas to increase the amount of staging of hydrogen into the system. Conduit 210*c* is provided to allow introduction of a second feed into the reactor; conduit 210*c* is shown with perforations 280*c* and also spargers (as an example of a distributor), indicated by arrows, with one or both present to distribute the second feed material so as to mix with the fluid (liquids and gases) flowing down from catalyst A. The combined fluids from conduit 210*c* and from the contact with catalyst A then contact catalyst B. Conduit 220*c*, which may be of the same or different design and material as conduit 210*c*, is provided to distribute a third feed material so as to mix with the fluids flowing down from catalyst B. As with conduit 210*c*, conduit 220*c* also is provided with perforations, as shown, and/or spargers, shown by arrows, as an example of a distributor), so as to facilitate mixing of the liquids and gases. The combined liquids flowing down the reactor 230*c* from catalyst B and from conduit 220*c* then contact catalyst C. The resultant effluent from contact of the fluids across catalyst C then leaves the reactor 230*c* via conduit 260*c*.

In an embodiment of the system illustrated by FIG. 2A, Catalyst A comprises a catalyst optimized for dealkylation of C10+ aromatic hydrocarbons, Catalyst B comprises a catalyst optimized for transalkylation of C7− and C9+ aromatic hydrocarbons, and Catalyst C comprises a catalyst optimized for cracking non-aromatic species. The feed introduced via 200*c* comprises C9+ aromatic hydrocarbons (such as a molar ratio of [benzene+toluene]/C9+ of about 10:90) with no more hydrogen gas than is sufficient to hydrogenate olefins produced in the dealkylation process to make light alkanes, such as an $H_2$:HC ratio of 1.5:1 or less, including as an option no hydrogen gas. The feed introduced into 210*c* comprises C7− (such as with a molar ratio of [benzene+toluene]/C9+ intermediate between the feed into 200*c* and 220*c* and a $H_2$:HC ratio also between the feed 200*c* and 220*c*. The feed introduced into 220*c* comprises C7− (such as with a molar ratio of [benzene+toluene]/C9+ at about 90:10) and an $H_2$:HC molar ratio of 0.5:1.0.

Figure 2B:
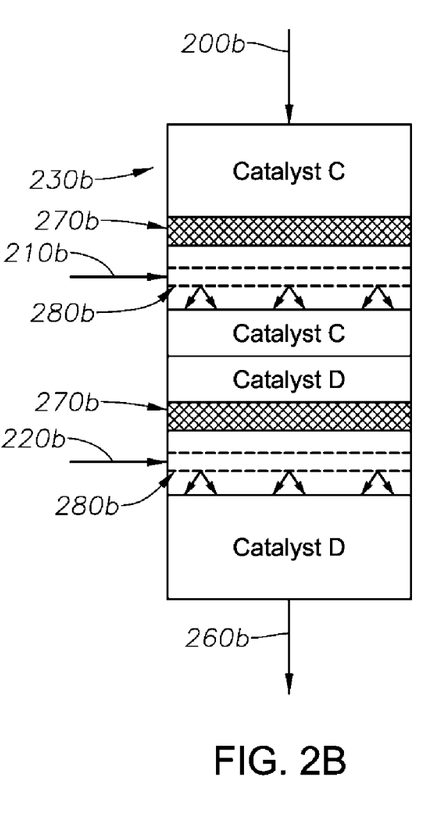

FIG. 2B shows reactor 230*b* from the same perspective as FIG. 2A, with conduit 200*b* at the top of the structure providing a feed to the reactor 230*b* so as to flow, such as by gravity, down the reactor 230*b* and out conduit 260*b* at the bottom, as reactor effluent, and containing a catalyst system comprising catalyst C, packed into two different beds, and catalyst D, also packed into two different beds. Such an arrangement allows increased staging of plural reactant feeds. Plural grid structures 270*b*, which may be of the type conventional in the art, and which may be the same or different throughout the reactor, are provided to support the solid catalysts, and also allow liquid and gas flowing down the reactor 230*b* to pass through and contact catalyst C and D, each in stages. One or more of the grid structures 270*b* may be used to introduce hydrogen gas to increase the amount of staging of hydrogen into the system. Conduit 210*b* is provided to allow introduction of a second feed (which may be liquid or gas or both) into the reactor; conduit 210*b* is shown with perforations 280*b* and also spargers (as an example of a distributor), indicated by arrows, with one or both present to distribute the second feed material so as to mix with the fluid (liquids and gases) flowing downstream from inlet 200*b* to outlet 260*b*. The combined fluids from conduit 210*b* and from the contact with the uppermost bed comprising catalyst C then contact the next bed of catalyst C and then the first bed of catalyst D. Conduit 220*b*, which may be of the same or different design and material as conduit 210*b*, is provided to distribute a third feed material, a fluid, liquid or gaseous or both, which may be the same or different from the first and/or second feed, so as to mix with the fluids flowing down from contact with catalyst D. As with conduit 210*b*, conduit 220*b* also is provided with perforations 280*b*, as shown, and/or spargers, shown by arrows, as an example of a distributor), so as to facilitate mixing of the liquids and gases. The combined liquids flowing down the reactor 230*b* from catalyst D and from conduit 220*b* then contact the second bed of catalyst D. The resultant effluent from contact of the fluids across the successive catalyst beds then leaves the reactor 230*b* via conduit 260*b*.

Figure 2C:
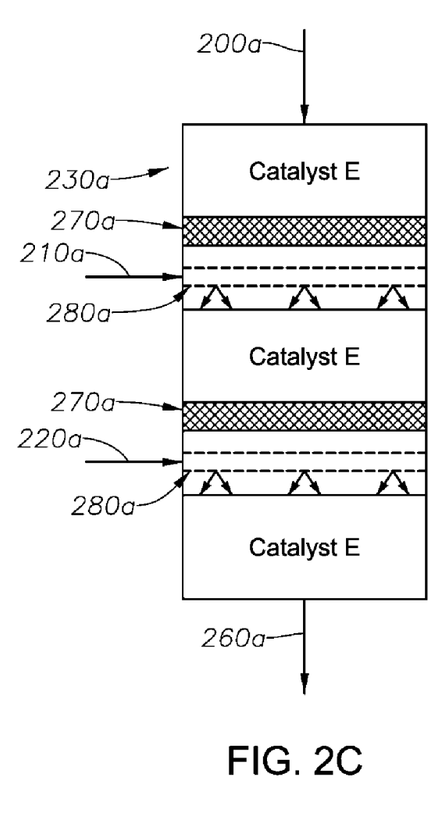

FIG. 2C illustrates yet another embodiment of the invention, wherein a first feed comprising most C9+ aromatic hydrocarbon is provided through inlet 200*a* to reactor 230*a* which comprises successive beds of catalyst E separated by plural grids 270*a*, and provided with conduits 210*a* and 220*a*, each with plural perforations 280*a* and/or spargers, shown by unnumbered plural arrows, to provide effluent 260*a*. This illustrates plainly the staged injection to a single catalyst system, which may be a single reactor out of several in series, such as illustrated in the next figure, FIG. 2D. Note that in one embodiment of the invention the transalkylation reaction envisioned may be one primarily concerned with converting benzene to toluene by reaction with C9+ aromatic hydrocarbons, which by way of illustration using FIG. 2C, would comprise the feeding of a feed comprising C9+ aromatic hydrocarbons and benzene (with perhaps only inevitable impurities of toluene) via conduit 200*a* into reactor 230*a* to contact successive beds of a transalkylation catalyst E, optimized for transalkylation of benzene and C9+ species to toluene. The inlets at 210*a* and 220*a* could then provide feeds with successively attenuated ratios of benzene:C9+ aromatic hydrocarbons and/or successively attenuated concentrations of hydrogen, to yield an effluent out of bottoms conduit 260*a*, rich in toluene. Such an arrangement, for instance, would be advantageously provided upstream of a reactor system for the conversion of toluene and methanol to xylenes, such as taught in U.S. application Ser. Nos. 13/875,373 and 13/875,402.

Figure 2D:
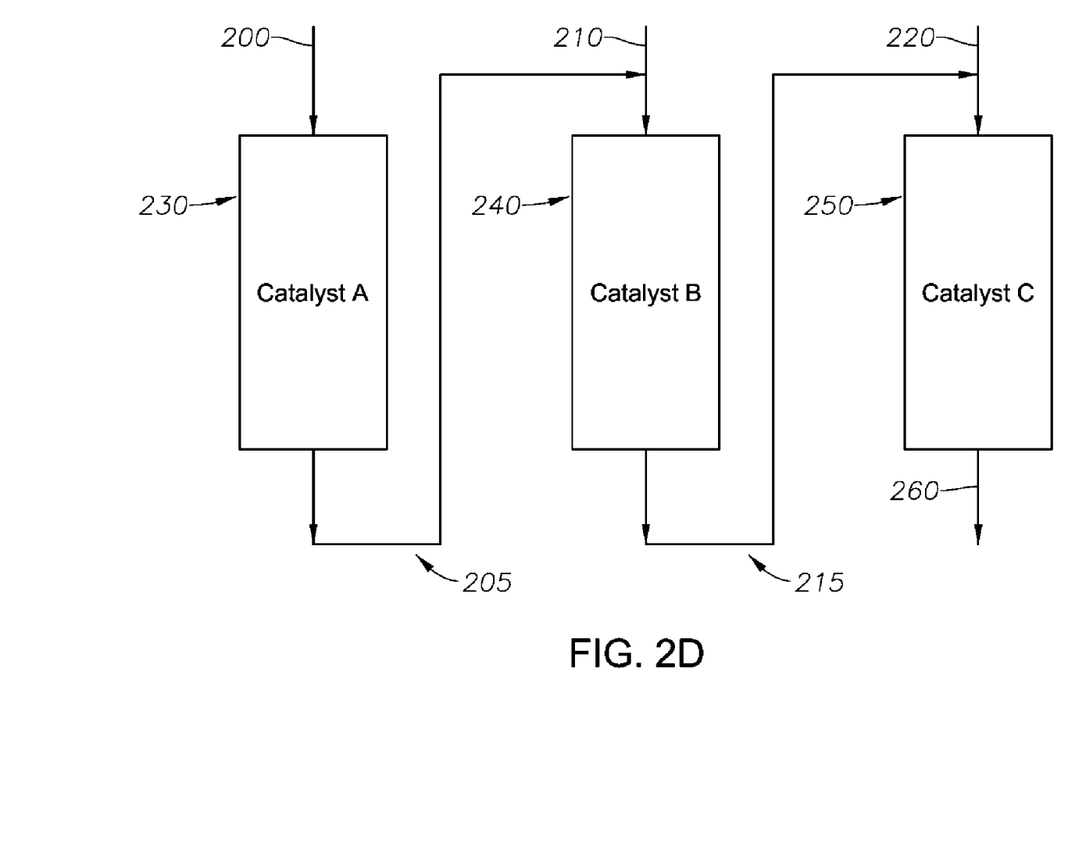

FIG. 2D illustrates a further embodiment of the inventions wherein successive catalysts A, B, and C, are provided in beds situated in separate reactors 230, 240, 250, respectively, in series. A first feed stream, such as one primarily comprising C9+ aromatic hydrocarbons, is provided to Catalyst A, preferably a catalyst for dealkylation of C10+ aromatic hydrocarbons, via conduit or inlet 200, and the effluent from the reactor, comprising an aromatic hydrocarbon stream having a decreased amount of C10+ aromatic hydrocarbon, is provided via conduit 205 to contact catalyst B in the presence of benzene and/or toluene provided via inlet or conduit 210. The effluent from reactor 240, preferably rich in xylenes (or rich in toluene, in the case where the preferred transalkylation product is toluene, such as just discussed in a previous example) is passed via conduit 215 to reactor 250 comprising catalyst C, which might be, for example, a catalyst for cracking of small alkanes and/or cyclic non-aromatic hydrocarbons. The species introduced via conduit 220 may be a diluent, with or without hydrogen, or it may be nothing at all.

One of skill in the art in possession of the present disclosure will recognize many additional advantages can be achieved. For instance, the hydrogen introduced into the reactor(s) can be staged based on the level of dealkylation achieved and the amount of alkyl aromatics in the feed stock. By reducing hydrogen partial pressures to the optimum, one can reduce ring loss and improve benzene purity.

By way of example, when the reactor feed to the first catalyst bed comprising a dealkylation catalyst is 80% C9+ aromatic hydrocarbon and 20% toluene and the targeted conversion are 90+% de-propylation and ~60% de-ethylation, it has been found that optimum hydrogen ratios are preferred to be based on the amount of alkyl groups that will be formed during the reaction rather than the total hydrocarbon, the latter being the conventional understanding. With the conventional approach there will be a wide variation in performance—catalyst life, ring loss, and benzene purity—as it is very likely excess hydrogen will be provided and optimum hydrogen is not achieved for both beds for changes in feed composition and severity. The present inventors have recognized that hydrogen be controlled based upon the amount of alkyl groups that are removed in the reaction. Furthermore, in order for the catalyst to saturate the ethylene and propylene formed in the dealkylation reactions a directionally higher metal function is preferred for long catalyst life and high conversions. By establishing the proper level of hydrogen undesired reactions may be minimized. It may be advantageous to operate the second and third beds after additional hydrogen injection to maximize life. In these beds the undesired side reaction are potentially less prevalent.

The invention has been described above with reference to numerous embodiments and specific examples. Many variations will suggest themselves to those skilled in this art in light of the above detailed description. All such obvious variations are within the full intended scope of the appended claims. Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. A process for producing xylenes by transalkylation comprising:
   (a) providing a reactor system comprising at least two catalysts, a first catalyst and a second catalyst, wherein said first catalyst is contained in a first bed and the second catalyst is contained in a second bed, said reactor system characterized by plural inlets for providing fluids to said reactor system;
   (b) introducing a first fluid comprising C9+ aromatic hydrocarbons at the location of said first catalyst, said first catalyst characterized as suitable for dealkylating at least a portion of said C9+ aromatic hydrocarbon, to provide a first product comprising (i) olefins; (ii) alkanes resulting from the saturation of said olefins; (iii) cycloalkanes; and (iv) a decreased amount of C10+ aromatic hydrocarbons having C2+ side chains, when compared with said first fluid; and
   (c) introducing a second fluid comprising benzene and/or toluene at the location of said second catalyst, in the presence of said first product, said second catalyst characterized as suitable for transalkylation of benzene and/or toluene and C9+ aromatic hydrocarbons to produce a second product comprising xylenes;
   the improvement comprising the staged injection of hydrogen to the first bed and second bed of said reactor system, whereby the amount of hydrogen present in step (b) is sufficient to increase the amount of alkanes resulting from the saturation of olefins and decrease the amount of cycloalkanes in said first product, wherein the amount of hydrogen is based on the amount of alkyl groups formed by the dealkylation,
   and further comprising reducing $H_2$:HC ratio in the first bed in response to benzene purity monitored downstream of said catalyst system for transalkylation.

2. The process of claim 1, wherein said second fluid comprises ≥90 mol % benzene, based on the amount of benzene and toluene in said second fluid.

3. The process of claim 1, wherein said second product is provided to an alkylation reactor for the conversion of aromatic hydrocarbons and methanol and/or dimethylether to xylenes.

4. The process of claim 1, and wherein the first bed is maintained at a temperature greater than said second bed.

5. The process of claim 1, wherein step (c) occurs in a reactor maintained at a temperature not exceeding 450° C.

6. The process of claim 1, wherein said second fluid in step (c) is introduced at a temperature lower than the temperature of said first product in step (b).

7. The process of claim 1, wherein said first bed is maintained at a temperature of about 393-427° C. and said second bed is maintained at a temperature of about 388-393° C.

8. The process of claim 1, wherein the $H_2$:HC ratio is attenuated in response to a change in the amount of alkyl aromatics introduced in step (b).

9. The process of claim 1, wherein:
   (i) said first catalyst comprises a molecular sieve having a Constraint Index in the range of about 3 to about 12 and about 0.01 to about 10 wt. %, based on the weight of the catalyst composition, of at least one hydrogenation component selected from Groups 6 to 12 of the Periodic Table of the Elements preferably present in an amount from about 0.01 to about 10 wt. % of the catalyst composition, and
   (ii) said second catalyst comprises a molecular sieve having a Constraint Index less than 3 and about 0.01 to about 10 wt. %, based on the weight of the catalyst composition, of at least one hydrogenation component selected from Groups 6 to 12 of the Periodic Table of the Elements.

10. The process of claim 9, further comprising a third catalyst bed, maintained under conditions effective to crack non-aromatic cyclic hydrocarbons in the effluent from the second catalyst bed, in the absence of all but inevitable amounts of hydrogen, said third catalyst bed comprising a molecular sieve having a Constraint Index from about 1 to 12.

11. The process of claim 9, wherein the molecular sieve of said first catalyst comprises ZSM-5 and the at least one hydrogenation component of said first catalyst is selected from the group consisting of platinum, palladium, iridium, rhenium, and mixtures thereof, and wherein the molecular sieve of said second catalyst comprises ZSM-12 and the at least one hydrogenation component of said first catalyst is selected from the group consisting of platinum, palladium, iridium, rhenium, and mixtures thereof.

12. The process of claim 10, wherein the molecular sieve of said third catalyst comprises ZSM-5.

* * * * *